United States Patent [19]

Oda et al.

[11] Patent Number: 5,331,011
[45] Date of Patent: Jul. 19, 1994

[54] N-BENZYL-N-PHENOXYETHYLAMINES AND AGRICULTURAL AND HORTICULTURAL BACTERICIDES

[75] Inventors: Mitsunori Oda; Kazutoshi Kikkawa; Akinori Tanaka; Satoko Imaruoka; Shigeo Yoshinaka, all of Niigata, Japan

[73] Assignee: Mitsubishi Gas Chemical Co., Inc., Tokyo, Japan

[21] Appl. No.: 43,854

[22] Filed: Apr. 7, 1993

Related U.S. Application Data

[62] Division of Ser. No. 691,798, Apr. 26, 1991, Pat. No. 5,221,694.

[30] Foreign Application Priority Data

Apr. 26, 1990 [JP] Japan .................. 2-108632

[51] Int. Cl.$^5$ .............. A01N 37/30; C07C 63/08; C07C 217/08
[52] U.S. Cl. .................... 514/555; 514/378; 514/448; 514/578; 514/554; 514/651; 548/248; 549/71; 562/493; 562/606; 562/607; 562/84; 564/347; 564/353; 564/354
[58] Field of Search ............ 564/353, 354, 352; 514/651, 378, 408, 461, 352, 357, 484, 559, 570, 574, 555; 554/103, 108; 562/8, 30, 45, 490, 493, 590; 558/166; 548/531, 532, 248; 546/314, 316; 549/76, 484

[56] References Cited

U.S. PATENT DOCUMENTS 3,959,359  5/1976  Pinhas .................. 514/651

FOREIGN PATENT DOCUMENTS 491880  6/1976  Australia.
433909  2/1968  Japan .................. 514/651

*Primary Examiner*—Shailendra Kumar
*Attorney, Agent, or Firm*—Sherman and Shalloway

[57] ABSTRACT

Disclosed is an N-benzyl-N-phenoxyethylamine selected from the group consisting of the N-benzyl-N-phenoxyethylamine represented by the following formula (I):

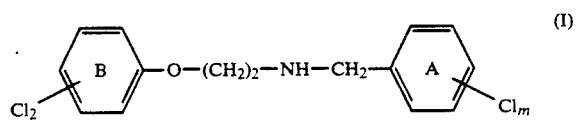

and an agriculturally acceptable acid addition salt represented by the following formula (II):

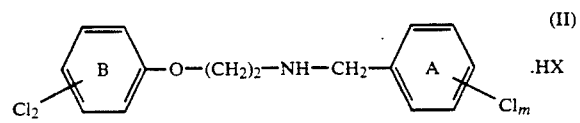

wherein m represents a number of 1 or 2 with a proviso that when m is 1 and a chlorine atom in the ring A is present at para(4)-position of the ring A, two chlorine atoms in the ring B are present at 2,3-, 2,5-, 2,6-, 3,4- or 3,5-positions of the ring B, and HX represents an acid.

11 Claims, No Drawings

N-BENZYL-N-PHENOXYETHYLAMINES AND AGRICULTURAL AND HORTICULTURAL BACTERICIDES

This is a division of application Ser. No. 07/691,798 filed Apr. 26, 1991, now U.S. Pat. No. 5,221,694.

BACKGROUND OF THE INVENTION (1) Field of the Invention

The present invention relates to novel N-benzyl-N-phenoxyethylamines and salts thereof, and to novel bactericides for agricultural and horticultural use.

(2) Description of the Prior Art

Inorganic copper-containing agents, organic copper-containing agents and antibiotic agents such as streptomycin have been used as bactericides for combating pathogenic bacteria causing blights in agricultural plants.

However, these conventional bactericides are defective in that the effect is practically insufficient and phytotoxicity is caused. Accordingly, development of a bactericide having strong bacteriostatic and bactericidal actions (both of the actions will be collectively called "antibacterial action" hereinafter) and having reduced phytotoxicity is desired at the present.

SUMMARY OF THE INVENTION

The present inventors have conducted a study in an effort to solve the above-mentioned problems inherent in the prior art and have arrived at the present invention which is capable of forming novel N-benzyl-n-phenoxyethylamines and salts thereof that exhibit antibacterial action that is strong enough for practical use with virtually no phytotoxicity.

According to the present invention, there is provided an N-benzyl-N-phenoxyethylamine selected from the group consisting of the N-benzyl-N-phenoxyethylamine represented by the following formula (I):

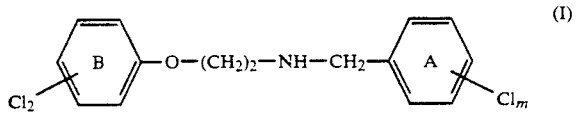

and an agriculturally acceptable acid addition salt represented by the following formula (II):

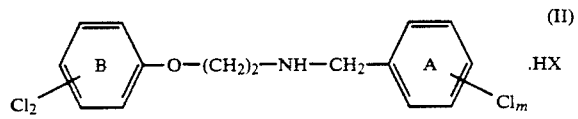

wherein m represents a number of 1 or 2 with a proviso that when m is 1 and a chlorine atom in the ring A is present at the para(4)-position of the ring A, two chlorine atoms in the ring B are present at 2,3-, 2,5-, 2,6-, 3,4- or 3,5-positions of the ring B, and HX represents an acid.

According to another embodiment of the present invention, there is provided an agricultural and horticultural bactericide comprising, as an active ingredient, an N-benzyl-N-phenoxyethylamine selected from the group consisting of the N-benzyl-N-phenoxyethylamine represented by the following formula (I'):

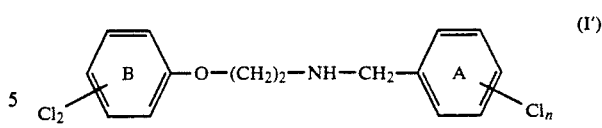

and an agriculturally acceptable acid addition salt represented by the following formula (II'):

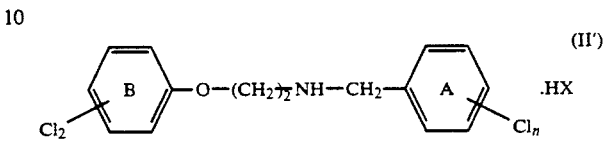

wherein n is a number of 1 or 2.

DT-OS 2429523 discloses an N-(4-chlorobenzyl)-N-(2,4-dichlorophenyl)-ethylamine which is a compound that resembles the N-benzyl-N-phenoxyethylamine of the present invention. As for the application of the above compound, however, the above publication simply describes to use the compound as an intermediate for synthesizing imidazole derivatives that are useful as bactericides. Namely, utilizability of the compounds of the general formulas (I) and (II) as bactericides was found by the present inventors.

DETAILED DESCRIPTION OF THE PREFERRED EMBODIMENT

The N-benzyl-N-phenoxyethylamine represented by the general formula I of the first invention is prepared, for example, as follows:

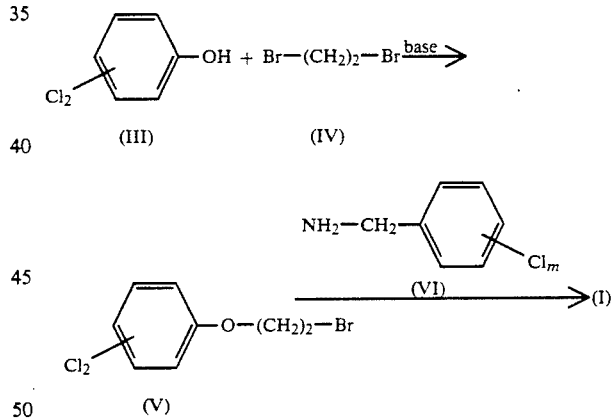

Namely, phenol III is reacted with dibromoethane IV in the presence of a base such as sodium hydroxide in a solvent such as water, an alcohol, dimethylsulfoxide or dimethylformamide to give phenoxyethyl bromide V, which is reacted with amine VI preferably in the presence of a hydrogen bromide scavenger in a solvent such as an alcohol, dimethylsulfoxide or dimethylformamide to give the N-benzyl-N-phenoxyethylamine I of the present invention.

The N-benzyl-N-phenoxyethylamine salt of the first invention represented by general formula II is prepared, for example, by reacting the above-mentioned N-benzyl-N-phenoxyethylamine I with an acid. Though there is no particular limitation on the kind of acid that is used, typical examples include hydrochloric acid, bromic acid, iodic acid, sulfuric acid, nitric acid, phosphoric acid, formic acid, acetic acid, propionic acid, butyric acid, isobutyric acid, valeric acid, pivalic acid, decanoic acid, lauric acid, oxalic acid, malonic acid, succinic acid, glutaric acid, adipic acid, maleic acid, fumaric acid, benzoic acid, phthalic acid, isophthalic acid, terephthalic acid, substituted benzoic acid, naphthoic acid, cinnamic acid, furancarboxylic acid, thiophenecarboxylic acid, pyrrolecarboxylic acid, pyridinecarboxylic acid, methanesulfonic acid, benzenesulfonic acid, p-methylbenzenesulfonic acid (p-toluenesulfonic acid), monobutylphosphoric acid ester, dibutylphosphoric acid ester, monobenzylphosphoric acid ester, dibenzylphosphoric acid, i, ester, 2-ethylhexylphosphoric acid ester, di(2-ethylhexyl)phosphoric acid ester, 3-phenyl-5-methylisoxazol-4-carboxylic acid and the like. Further, the acid may be used in either the gaseous state or the liquid state.

In the general formula II, HX corresponds to the acid used in the preparation.

In the preparation of salt, use of a reaction solvent is not absolutely necessary, but a solvent ordinarily used as a reaction solvent, such as, an alcohol, an ether or an ester, or water, can be used as the reaction solvent. Though there is no particular limitation on the reaction temperature, when, for example, a mineral acid is used in the gaseous form, the loss of mineral can be decreased by maintaining the temperature as low as, for example, at 0° C.

The N-benzyl-N-phenoxyethylamine salt of the first invention is solid or liquid at room temperature or normal temperature, and, in the case of solid, the salt can be recovered from the reaction product liquor by ordinary solid-liquid separating means such as filtration or centrifugal separation and if desired, the recovered crystals can be purified by washing or recrystallization from an alcohol or water.

The physical properties of the N-benzyl-N-phenoxyethylamine represented by general formula I and the N-benzyl-N-phenoxyethylamine salt represented by general formula II of the present invention are shown in Tables 1 and 2, respectively.

TABLE 1

Physical properties of N-benzyl-N-phenoxyethylamines.

First line: compound No. Cl(phenoxy group), $Cl_m$
Second and subsequent line;   ① state, melting point
                              ② NMR values $^1$H-NMR(CDCL$_3$) δppm 1   2,4-$Cl_2$   2-Cl
①   colorless columnar crystal m.p. 54~55° C.
②   2.05(s, 1H), 3.01(t, J=5Hz, 2H), 3.93(s, 2H), 4.07(t, J=5Hz, 2H), 6.73(d, J=9Hz, 1H), 7.11(dd, J=9, 2Hz, 1H), 7.2-7.5(m, 5H)

2   2,4-$Cl_2$   3-Cl
①   colorless oil m.p. (hydrochloride) 135~137° C.
②   1.76(s, 1H), 3.01(t, J=5Hz, 2H), 3.85(s, 2H), 4.09(t, J=5Hz, 2H), 6.79(d, J=9Hz, 1H), 7.14(dd, J=9, 2Hz, 1H), 7.20(s, 4H), 7.32(d, J=2Hz, 1H)

3   2,4-$Cl_2$   3,4-$Cl_2$
①   colorless needle crystal m.p. 42~43° C.
②   1.87(s, 1H), 2.99(t, J=5Hz, 2H), 3.81(s, 2H), 4.07(t, J=5Hz, 2H), 6.75(d, J=8Hz, 1H), 7.0-7.4(m, 5H)

4   3,4-$Cl_2$   2-Cl
①   colorless columnar crystal m.p. 64~66° C.
②   1.91(s, 1H), 3.00(t, J=5Hz, 2H), 3.93(s, 2H), 4.07(t, J=5Hz, 2H), 6.67(dd, J=9, 2.5Hz, 1H), 6.93(d, J=2.5Hz, 1H), 7.1-7.5(m, 5H)

5   3,4-$Cl_2$   3-Cl
①   colorless oil m.p. (hydrochloride) 180~182° C.
②   1.75(s, 1H), 2.97(t, J=5Hz, 2H), 3.81(s, 2H), 4.01(t, J=5Hz, 2H), 6.68(dd, J=9, 2.5Hz, 1H), 6.95(d, J=2.5Hz, 1H), 7.1-7.3(m, 5H)

6   3,4-$Cl_2$   4-Cl
①   colorless needle crystal m.p. 63~65° C.

TABLE 1-continued

Physical properties of N-benzyl-N-phenoxyethylamines.

②   1.76(s, 1H), 2.96(t, J=5Hz, 2H), 3.80(s, 2H), 4.00(t, J=5Hz, 2H), 6.69(dd, J=9, 2.5Hz, 1H), 6.94(d, J=2.5Hz, 1H), 7.23(s, 4H), 7.29(d, J=9Hz, 1H)

7   3,4-$Cl_2$   2,4-$Cl_2$
①   colorless columnar crystal m.p. 37~39° C.
②   1.83(s, 1H), 3.00(t, J=5Hz, 2H), 3.82(s, 2H), 4.06(t, J=5Hz, 2H), 6.73(dd, J=9, 2.5Hz, 1H), 6.98(d, J=2.5Hz, 1H), 7.1-7.4(m, 4H)

8   3,4-$Cl_2$   3,4-$Cl_2$
①   colorless oil m.p. (hydrochloride) 154~156° C.
②   1.76(s, 1H), 2.97(t, J=5Hz, 2H), 3.80(s, 2H), 4.05(t, J=5Hz, 2H), 6.67(dd, J=8, 2Hz, 1H), 6.9-7.4(m, 5H)

9   2,5-$Cl_2$   3,4-$Cl_2$
①   colorless needle crystal m.p. 34~36° C.
②   2.61(s, 1H), 3.00(t, J=5Hz, 2H), 3.81(s, 2H), 4.08(t, J=5Hz, 2H), 6.7-7.5(m, 6H)

10   2.6-$Cl_2$   3,4-$Cl_2$
①   colorless oil m.p. (hydrochloride) 162~164° C.
②   2.10(s, 1H), 2.98(t, J=5Hz, 2H), 3.80(s, 2H), 4.13(t, J=5Hz, 2H), 6.7-7.5(m, 6H)

11   2,3-$Cl_2$   3,4-$Cl_2$
①   colorless columnar crystal m.p. 52~53° C.
②   1.84(s, 1H), 2.97(t, J=5Hz, 2H), 3.81(s, 1H), 4.10(t, J=5Hz, 2H), 6.73(dd, J=8, 3.5Hz, 1H), 7.0-7.5(m, 5H)

12   3,5-$Cl_2$   3,4-$Cl_2$
①   colorless columnar crystal m.p. 29~30° C.
②   1.40(s, 1H), 2.97(t, J=5Hz, 2H), 3.80(s, 2H), 4.05(t, J=5Hz, 2H), 6.73(d, J=1.5Hz, 2H), 6.89(t, J=1.5Hz, 1H), 7.13(dd, J=8, 1.5Hz, 1H), 7.29(d, J=1.5Hz, 1H), 7.34(d, J=8Hz, 1H)

13   2,3-$Cl_2$   2,4-$Cl_2$
①   colorless columnar crystal m.p. 84~86° C.
②   1.97(s, 1H), 3.03(t, J=5Hz, 2H), 3.92(s, 2H), 4.13(t, J=5Hz, 2H), 6.25(dd, J=7, 3Hz, 1H), 7.0-7.5(m, 5H)

14   3,5-$Cl_2$   2,4-$Cl_2$
①   colorless columnar crystal m.p. 36~38° C.
②   2.02(s, 1H), 2.93(t, J=5Hz, 2H), 3.75(s, 2H), 3.97(t, J=5Hz, 2H), 6.68(d, J=1.5Hz, 2H), 6.81(t, J=1.5Hz, 1H), 7.06(dd, J=9, 1.5Hz, 1H), 7.24(d, J=9Hz, 1H), 7.36(d, J=1.5Hz, 1H)

15   3,4-$Cl_2$   2.6-$Cl_2$
①   colorless oil m.p. (hydrochloride) 196~198° C.
②   2.06(s, 1H), 2.97(t, J=5Hz, 2H), 3.97(t, J=5Hz, 2H), 4.09(s, 2H), 6.66(dd, J=9, 3Hz, 1H), 6.91(d, J=3Hz, 1H), 7.0-7.3(m, 4H)

16   2,3-$Cl_2$   2.6-$Cl_2$
①   colorless needle crystal m.p. 77~78° C.
②   1.33(s, 1H), 3.05(t, J=5Hz, 2H), 4.10(t, J=5Hz, 2H), 4.15(s, 2H), 6.71(dd, J=6, 4Hz, 1H), 6.9-7.4(m, 5H)

17   3,5-$Cl_2$   2.6-$Cl_2$
①   colorless columnar crystal m.p. 46~47° C.
②   2.04(s, 1H), 3.00(t, J=5Hz, 2H), 4.00(t, J=5Hz, 2H), 4.13(s, 2H), 6.08(d, J=1.5Hz, 1H), 6.90(t, J=1.5Hz, 1H), 7.23(m, 3H)

18   2,6-$Cl_2$   2.6-$Cl_2$
①   colorless columnar crystal m.p. 50~52° C.
②   2.39(s, 1H), 3.07(t, J=5Hz, 2H), 4.18(t, J=5Hz, 2H), 4.19(s, 2H), 6.8-7.4(m, 3H)

19   2,5-$Cl_2$   2.6-$Cl_2$
①   colorless needle crystal m.p. 71~73° C.
②   2.30(s, 1H), 3.06(t, J=5Hz, 2H), 4.09(t, J=5Hz, 2H), 4.15(s, 2H), 6.7-7.0(m, 2H), 7.1-7.4(m, 2H)

20   2,4-$Cl_2$   2.6-$Cl_2$
①   colorless oil m.p. (hydrochloride) 190~192° C.
②   2.33(s, 1H), 3.03(t, J=5Hz, 2H), 4.05(t, J=5Hz, 2H), 4.12(s, 2H), 6.71(d, J=9Hz, 1H), 7.0-7.3(m, 5H)

21   3.4-$Cl_2$   2,3-$Cl_2$
①   colorless oil m.p. (hydrochloride) 175~177° C.
②   1.98(s, 1H), 3.00(t, J=5Hz, 2H), 3.96(s, 2H), 4.05(t, J=5Hz, 2H), 6.71(dd, J=9.2Hz, 1H), 6.98(d, J=2Hz, 1H), 7.1-7.5(m, 4H)

22   2,3-$Cl_2$   2,3-$Cl_2$
①   colorless columnar crystal m.p. 105~106° C.
②   1.98(brs, 1H), 3.04(t, J=5Hz, 2H), 4.01(s, 2H), 4.16(t, J=5Hz, 2H), 6.7-7.5(m, 6H)

23   2,6-$Cl_2$   2,3-$Cl_2$
①   colorless oil m.p. (hydrochloride) 148~150° C.

TABLE 1-continued

Physical properties of N-benzyl-N-phenoxyethylamines.

② 2.21(s, 1H), 3.07(t, J=5Hz, 2H), 4.01(s, 2H),
4.20(t, J=5Hz, 2H), 6.8-7.4(m, 6H)
24 2,4-Cl₂ 2,3-Cl₂
① colorless oil m.p. (hydrochloride) 189~191° C.
② 2.96(s, 1H), 3.05(t, J=5Hz, 2H), 4.00(s, 2H),
4.12(t, J=5Hz, 2H), 6.82(d, J=9Hz, 1H),
7.0-7.5(m, 5H)
25 3,5-Cl₂ 2,3-Cl₂
① colorless oil m.p. (hydrochloride) 172~174° C.
② 1.90(s, 1H), 3.00(t, J=5Hz, 2H), 3.96(s, 2H),
4.05(t, J=5Hz, 2H), 6.76(d, J=2Hz, 2H),
6.92(t, J=2Hz, 1H), 7.30(m, 3H)
26 2,5-Cl₂ 2,3-Cl₂
① colorless columnar crystal m.p. 67~69° C.
② 2.08(s, 1H), 3.05(t, J=5Hz, 2H), 3.99(s, 2H),
4.12(t, J=5Hz, 2H), 6.7-7.5(m, 6H)
27 3,4-Cl₂ 3,5-Cl₂
① colorless oil m.p. (hydrochloride) 199~201° C.
② 1.80(s, 1H), 2.97(t, J=5Hz, 2H), 3.80(s, 2H),
4.03(t, J=5Hz, 2H), 6.67(dd, J=9, 2.5Hz, 1H),
6.98(d, J=2.5Hz, 1H), 7.23(s, 3H), 7.34(d, J=9Hz, 1H)
28 2,3-Cl₂ 3,5-Cl₂
① colorless oil m.p. (hydrochloride) 163~165° C.
② 1.77(s, 1H), 2.99(t, J=5Hz, 2H), 3.83(s, 2H),
4.06(t, J=5Hz, 2H), 6.79(d, J=1.8Hz, 2H),
6.97(d, J=1.8Hz, 1H), 7.25(s, 3H)
29 2,4-Cl₂ 3,5-Cl₂
① colorless oil m.p. (hydrochloride) 171~172° C.
② 1.90(s, 1H), 3.00(t, J=5Hz, 2H), 3.84(s, 2H),
4.11(t, J=5Hz, 2H), 6.81(d, J=9Hz, 1H),
7.18(dd, J=9, 2.5Hz, 1H), 7.24(s, 3H)
7.35(d, J=2.5Hz, 1H)
30 3,5-Cl₂ 3,5-Cl₂
① colorless oil m.p. (hydrochloride) 171~172° C.
② 1.83(s, 1H), 3.03(t, J=5Hz, 2H), 3.87(s, 2H),
4.14(t, J=5Hz, 2H), 6.7-7.2(m, 3H), 7.25(s, 3H)
31 2,6-Cl₂ 3,5-Cl₂
① colorless oil m.p. (hydrochloride) 154~156° C.
② 2.07(s, 1H), 3.03(t, J=5Hz, 2H), 3.86(s, 2H),
4.20(t, J=5Hz, 2H), 6.8-7.4(m, 6H)
32 2,5-Cl₂ 3,5-Cl₂
① colorless oil m.p. (hydrochloride) 186~187° C.
② 1.99(s, 1H), 3.04(t, J=5Hz, 2H), 3.86(s, 2H),
4.13(t, J=5Hz, 2H), 6.8-7.0(m, 2H), 7.28(s, 3H),
7.29(d, J=9Hz, 1H)
33 3,4-Cl₂ 2,5-Cl₂
① colorless oil m.p. (hydrochloride) 153~155° C.
② 1.94(s, 1H), 3.01(t, J=5Hz, 2H), 3.90(s, 2H),
4.05(t, J=5Hz, 2H), 6.72(dd, J=9, 3Hz, 1H),
6.98(d, J=3Hz, 1H), 7.2-7.5(m, 4H)
34 2,4-Cl₂ 2,5-Cl₂
① colorless oil m.p. (hydrochloride) 204~205° C.
② 2.04(s, 1H), 3.00(t, J=5Hz, 2H), 3.90(s, 2H),
4.11(t, J=5Hz, 2H), 6.73(d, J=9Hz, 1H),
7.0-7.4(m, 5H)
35 2,5-Cl₂ 2,5-Cl₂
① colorless oil m.p. (hydrochloride) 191~192° C.
② 2.22(s, 1H), 3.06(t, J=5Hz, 2H), 3.93(s, 2H),
4.02(t, J=5Hz, 2H), 6.8-6.9(m, 2H), 7.2-7.3(m, 3H),
7.46(d, J=2Hz, 1H)
36 2,3-Cl₂ 2,5-Cl₂
① colorless columnar crystal m.p. 58~60° C.
② 2.05(s, 1H), 3.05(t, J=5Hz, 2H), 3.92(s, 2H),
4.17(t, J=5Hz, 2H), 6.76(dd, J=7, 4Hz, 1H),
7.0-7.3(m, 4H), 7.45(d, J=2Hz, 1H)
37 2,6-Cl₂ 2,5-Cl₂
① colorless oil m.p. (hydrochloride) 192~193° C.
② 2.22(s, 1H), 3.02(t, J=5Hz, 2H), 3.90(s, 2H),
4.16(t, J=5Hz, 2H), 6.7-7.3(m, 5H),
7.15(d, J=2Hz, 1H)
38 3,5-Cl₂ 2,5-Cl₂
① colorless oil m.p. (hydrochloride) 48~49° C.
② 1.92(s, 1H), 3.00(t, J=5Hz, 2H), 3.89(s, 2H),
4.04(t, J=5Hz, 2H), 6.73(d, J=2Hz, 2H),
6.89(t, J=2Hz, 1H), 7.18(m, 2H), 7.41(d, J=2Hz, 1H)

TABLE 2

Physical properties of N-benzyl-N-phenoxyethylamine salts

| Compound No. | Cl (phenoxy group) | $Cl_m$ | HX | mp (°C.) |
|---|---|---|---|---|
| 39 | 2,4-Cl₂ | 3-Cl | HCl | 135~137 |
| 40 | 3,4-Cl₂ | 2-Cl | HCl | 179~181 |
| 41 | 3,4-Cl₂ | 3-Cl | HCl | 188~190 |
| 42 | 3,4-Cl₂ | 4-Cl | HCl | 183~185 |
| 43 | 3,4-Cl₂ | 2,4-Cl₂ | HCl | 182~186 |
| 44 | 3,4-Cl₂ | 3,4-Cl₂ | HCl | 154~156 |
| 45 | 3,4-Cl₂ | 3,4-Cl₂ | HBr | 187~188 |
| 46 | 3,4-Cl₂ | 3,4-Cl₂ | HI | 192~193 |
| 47 | 3,4-Cl₂ | 3,4-Cl₂ | HNO₃ | 189~190 |
| 48 | 3,4-Cl₂ | 3,4-Cl₂ | H₂SO₄ | 159~160 |
| 49 | 3,4-Cl₂ | 3,4-Cl₂ | H₃PO₄ | 164~167 |
| 50 | 2,6-Cl₂ | 3,4-Cl₂ | HCl | 162~164 |
| 51 | 2,3-Cl₂ | 3,4-Cl₂ | HCl | 184~186 |
| 52 | 3,5-Cl₂ | 3,4-Cl₂ | HCl | 166~167 |
| 53 | 2,3-Cl₂ | 2,4-Cl₂ | HCl | 188~190 |
| 54 | 3,5-Cl₂ | 2,4-Cl₂ | HCl | 168~170 |
| 55 | 3,4-Cl₂ | 2,6-Cl₂ | HCl | 196~198 |
| 56 | 2,3-Cl₂ | 2,6-Cl₂ | HCl | 187~189 |
| 57 | 3,5-Cl₂ | 2,6-Cl₂ | HCl | 194~196 |
| 58 | 2,6-Cl₂ | 2,6-Cl₂ | HCl | 196~198 |
| 59 | 2,5-Cl₂ | 2,6-Cl₂ | HCl | 202~204 |
| 60 | 2,4-Cl₂ | 2,6-Cl₂ | HCl | 190~192 |
| 61 | 3,4-Cl₂ | 2,3-Cl₂ | HCl | 175~177 |
| 62 | 2,3-Cl₂ | 2,3-Cl₂ | HCl | 171~173 |
| 63 | 2,6-Cl₂ | 2,3-Cl₂ | HCl | 148~150 |
| 64 | 2,4-Cl₂ | 2,3-Cl₂ | HCl | 189~191 |
| 65 | 3,5-Cl₂ | 2,3-Cl₂ | HCl | 172~174 |
| 66 | 2,5-Cl₂ | 2,3-Cl₂ | HCl | 159~161 |
| 67 | 3,4-Cl₂ | 3,5-Cl₂ | HCl | 199~201 |
| 68 | 2,3-Cl₂ | 3,5-Cl₂ | HCl | 163~165 |
| 69 | 2,4-Cl₂ | 3,5-Cl₂ | HCl | 171~172 |
| 70 | 3,5-Cl₂ | 3,5-Cl₂ | HCl | 171~172 |
| 71 | 2,6-Cl₂ | 3,5-Cl₂ | HCl | 154~156 |
| 72 | 2,5-Cl₂ | 3,5-Cl₂ | HCl | 186~187 |
| 73 | 3,4-Cl₂ | 2,5-Cl₂ | HCl | 153~155 |
| 74 | 2,4-Cl₂ | 2,5-Cl₂ | HCl | 204~206 |
| 75 | 2,5-Cl₂ | 2,5-Cl₂ | HCl | 191~192 |
| 76 | 2,3-Cl₂ | 2,5-Cl₂ | HCl | 161~163 |
| 77 | 2,6-Cl₂ | 2,5-Cl₂ | HCl | 192~193 |
| 78 | 3,5-Cl₂ | 2,5-Cl₂ | HCl | 180~182 |
| 79 | 2,3-Cl₂ | 3,4-Cl₂ | * | 188~189 |
| 80 | 2,3-Cl₂ | 3,4-Cl₂ | ** | 97 98 |
| 81 | 3,4-Cl₂ | 2-Cl | * | 164 166 |
| 82 | 3,4-Cl₂ | 4-Cl | * | 94 95 |
| 83 | 3,4-Cl₂ | 3,4-Cl₂ | * | 173 175 |
| 84 | 3,4-Cl₂ | 3,4-Cl₂ | *** | 112 113 |
| 85 | 3,4-Cl₂ | 3,4-Cl₂ | **** | 94 95 |
| 86 | 3,4-Cl₂ | 3,4-Cl₂ | Benzoic acid | 108 110 |
| 87 | 3,4-Cl₂ | 3,4-Cl₂ | *** | 134 135 |
| 88 | 3,4-Cl₂ | 3,4-Cl₂ | Propionic acid | 64 65 |
| 89 | 3,4-Cl₂ | 3,4-Cl₂ | Acetic acid | 72 74 |
| 90 | 2,5-Cl₂ | 3,4-Cl₂ | * | 168 170 |
| 91 | 3,5-Cl₂ | 3,4-Cl₂ | * | 140 146 |
| 92 | 3,5-Cl₂ | 3,4-Cl₂ | ** | 111 113 |
| 93 | 3,5-Cl₂ | 3,4-Cl₂ | Benzoic acid | 89 91 |

*p-toluenesulfonic acid
**2-thiophene carboxylic acid
***3-phenyl-5-methylisoxazol-4-carboxylic acid
****m-trifluoromethyl benzoic acid According to the second invention, furthermore, there is provided an agricultural and horticultural bactericide which comprises as an active ingredient at least one of the N-benzyl-N-phenoxyethylamine compounds represented by the general formula I' and a salt of the N-benzyl-N-phenoxyethylamine represented by the general formula II':

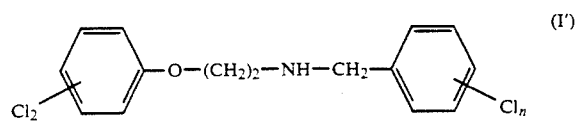

(I')

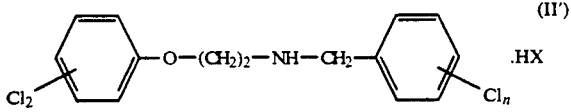

wherein in the general formulas I' and II', n is 1 or 2, and in the general formula II', HX represents an acid.

The N-benzyl-N-phenoxyethylamine represented by the general formula I' and N-benzyl-N-phenoxyethylamine salt represented by the general formula II' (hereinafter the N-benzyl-N-phenoxyethylamine and a salt thereof are often collectively referred to as N-benzyl-N-phenoxyethylamines) exhibit strong antibacterial action against bacteria belonging to the genus Xanthomonas such as bacteria causing citrus canker and bacteria belonging to the genus Clavibacter such as bacteria causing tomato canker, as well as against bacteria causing blights in agricultural plants. Phytotoxicity when these compounds are used is smaller than that of when conventional chemical agents are used. Further, the N-benzyl-N-phenoxyethylamines all remain chemically stable and can be preserved for extended periods of time.

Therefore, the agricultural and horticultural bactericide of the second invention that comprises these N-benzyl-N-phenoxyethylamine as active ingredients, exhibits strong antibacterial action against a variety of pathogenic bacteria with little phytotoxicity, and can be preserved for extended periods of time.

The agricultural and horticultural bactericide of the second invention is effective for controlling a variety of blights caused by various pathogenic bacteria such as citrus canker, bacterial leaf blight of rice, bacterial shot hole of peach, black rot of cabbage, bacterial blight of lettuce, bacterial spot of melon, leaf blight of soy bean, and tomato canker.

A preferred example of the active ingredient of the agricultural and horticultural bactericide of the second invention is a salt of the N-benzyl-N-phenoxyethylamine that exhibits stronger antibacterial action and that is more stable than the N-benzyl-N-phenoxyethylamine, and that can be easily recovered during preparation.

The agricultural and horticultural bactericide of the second invention can be formed into an optional preparation of an agricultural and horticultural agent, such as a wettable powder, a liquid, an emulsifiable concentrate, a flowable (sol) preparation, a powder, a driftless (DL) dust or a granule by the method known per sex using the novel compound of the first invention. The carrier to be used for such preparations is not particularly critical, and any of carrier customarily used in this field can be used. As typical examples of the solid carrier, there can be mentioned mineral powders such as kaolin, bentonire, clay, talc and vermiculite, plant powders such as wood meal, starch and crystalline cellulose, and polymeric compounds such as a petroleum resin, polyvinyl chloride, a ketone resin and dammar gum. As typical examples of the liquid carrier, there can be mentioned water, alcohols such as methyl alcohol, ethyl alcohol, n-propyl alcohol, isopropyl alcohol, butanol, ethylene glycol and benzyl alcohol, aromatic hydrocarbons such as toluene, benzene, xylene, ethylbenzene and methylnaphthalene, halogenated hydrocarbons such as chloroform, carbon tetrachloride, dichloromethane, chloroethylene, monochlorobenzene, trichlorofluoromethane and dichlorofluoromethane, ethers such as ethyl ether, ethylene oxide and dioxane, ketones such as acetone, methyl ethyl ketone, cyclohexanone and methyl isobutyl ketone, esters such as ethyl acetate, butyl acetate and ethylene glycol acetate, acid amides such as dimethylformamide and dimethylacetamide, sulfoxides such as dimethylsulfoxide, alcohol ethers such as ethylene glycol monomethylether and ethylene glycol monoethyl ether, aliphatic and alicyclic hydrocarbones such as n-hexane and cyclohexane, gasolines of the industrial grade such as petroleum ether and solvent naphtha, paraffins, and petroleum fractions such as kerosene and gas oil.

Various surface active agents can be used. As typical instances of the surface active agent, there can be mentioned nonionic surface active agents such as polyoxyethylene alkyl ether and polyoxyethylene alkyl ester, anionic surface active agents such as alkyl benzene-sulfonate and alkyl sulfate, cationic surface active agents such as lauryl and stearyltrimethyl ammonium chlorides, and amphoteric surface active agents such as betaine type carboxylic acid and sulfuric acid esters.

The content of the compound of the first invention in a preparation as mentioned above is not particularly critical, but from a practical viewpoint, the content of the compound is generally about 0.001 to about 95% by weight (expressed as the compound of general formula I; the same will apply hereinafter) and preferably about 0.01 to about 90% by weight. Practically, in the case of a powder, a DL dust and a granule, the content of the compound of the present invention is about 0.01 to about 5% by weight, and in the case of a wettable powder, a liquid and an emulsifiable concentrate, the content of the compound of the present invention is about 1 to 75% by weight.

The so-formed preparation, for example, a powder, a driftless dust or a granule, is directly applied, and a wettable powder, a liquid, an emulsifiable concentrate or a flowable agent is applied after it has been diluted with water or an appropriate solvent.

The rate of application of the agricultural and horticultural bactericide of the second invention varies depending on the kind of the disease to be controlled, the degree of the disease, the kind of the plant to be treated, the region of application, the method of application, the season of application and the kind of preparation, and cannot be exclusively specified. However, the active ingredient or the compound represented by the general formula I of the first invention (or the compound that is represented by the general formula II of the first invention is reckoned as that of the general formula I) is used in an amount of 2 to 6 kg per 10 ares in the case of a powder, driftless dust or granule (the concentration of the active ingredient is 3% by weight) or in an amount of 0.05 to 3 kg being diluted in 100 to 500 liters of water in the case of a wettable powder, liquid, emulsifiable concentrate or flowable agent (the concentration of the active ingredient is 20% by weight).

The compound of the first invention and, particularly, the compound represented by the general formula II exhibits strong antibacterial action and improved stability, and can be applied over extended periods of seasons, and can be desirably used as an agricultural and horticultural agent.

Examples

The present invention will now be concretely described with reference to the following examples that by no means limit the scope of the invention.

EXAMPLE 1

Synthesis of N-3,4-dichlorobenzyl-N-2-(3,4-dichlorophenoxy)ethylamine (compound No. 8).

5.40 Grams (20.0 mmol) of 2-(3,4-dichlorophenoxy)ethyl bromide was dissolved in 50 ml of isopropyl alcohol, followed by addition of 4.26 g (40.0 mmol) of anhydrous sodium carbonate and 6.30 g (35.8 mmol) of 3,4-dichlorobenzylamine. The mixture was refluxed for 8 hours on an oil bath. After cooling, the reaction mixture was poured into 200 ml of water and was extracted with chloro form ( 4 0 ml×3).

The organic layer was dried over with magnesium sulfate and the solvent was removed by distillation, and the residue was purified by silica gel column chromatography ( developing agent: ethyl acetate/chloroform=4/6) to give the captioned compound in an amount of 5.89 g (yield; 81%) in the form of a colorless oil.

The compound exhibited the following properties.
$^{13}$C-NMR (CDCl$_3$);

47.90(t), 52.47(t), 68.21(t), 1 14.46(d), 116.44(d), 124.09(s), 127.24(d) , 129.80(d), 130.22(d), 130.59(d), 130.74(s), 132.36(s), 132.78(s), 140.53(s), 157.76(s)ppm Infrared absorption spectrum (liquid. film method);

$\nu$max=2820$^m$, 1580$^s$, 1560$^s$, 1445$^s$, 1255$^s$, 1220$^s$, 1115$^s$, 1020$^s$, 800$^s$, 655$^s$cm$^{-1}$ Mass spectrum;

m/e=369(M$^+$+6.1% ), 368(M$^+$+5.1%), 367(M$^+$+4.4% ), 366(M$^+$+3.2%), 365(M$^+$+2.8% ), 364(M$^+$+1.1% ), 363(M$^+$+6% ), 204(3%), 202(5%), 192(11%), 191(7%), 190(64%), 189(11%), 188(98%), 163(13%), 162(7%), 161(70%), 160(9%), 159(100%), 126(3%), 124(6%), 123(8%).

Ultraviolet absorption spectrum (EtOH);

$\nu$max=202(60,900), 219$^{sh}$(17,100), 228$^{sh}$(15,000), 276$^{sh}$(1,230), 282(1,830), 291(1,460)nm Elementary analysis;

calculated as C$_{15}$H$_{13}$Cl$_4$NO C:49.35 H:3.59 N:3.84(%) Found; C:49.59 H:3.53 N:4.09(%)

EXAMPLE 2

Synthesis of N-3-chlorobenzyl-N-2-( 2,4-dichlorophenoxy)ethylamine ( compound No. 2).

2.70 Grams (10.0 retool) of 2-(2,4-dichlorophenoxy)ethyl bromide was dissolved in 30 ml of ethanol, followed by the addition of 1.06 g (10.0 mmol) of anhydrous sodium carbonate and 4.25 g (30.0 mmol) of 3-chlorobenzylamine. The mixture was refluxed for 6 hours on an o il bath. After cooling, the reaction mixture was poured into 100 ml of water and was extracted with chloroform (20 ml×3).

The organic layer was d ried over with magnesium sulfate and the solvent was removed by distillation, and the residue was purified by silica gel column chromatography (developing agent: ethyl acetate/chloroform=1/1) to give the captioned compound in an amount of 2.51 g ( yield; 76% ) in the form of a colorless oil.

The compound exhibited the following properties.
$^{13}$C-NMR (CDCl$_3$);

47.75(t), 53.02(t), 69.30(t), 114.37(d), 123.88(s), 125.99(d), 126.75(s), 127.02(d), 127.51(d), 128.00(d), 129.55(d), 129.86(d), 134.25(s), 142.30(s), 153.09(s)ppm Infrared absorption spectrum (liquid film method);

$\nu$max=2830$^m$, 1575$^s$, 1455$^s$, 1250$^s$, 1100$^s$, 1060$^s$, 1035$^s$, 865$^s$, 800$^s$, 775$^s$, 735$^s$, 680$^s$cm$^{-1}$ Mass spectrum;

m/e=330(M$^+$+1.1%), 298(5%), 297(6%), 296(25%), 295(19%), 294(36%), 293(19%), 170(2%), 169(2%), 168(5%), 157(3%), 156(30%), 155(9%), 154(90%), 128(3%), 127(34%), 126(10%), 125(100%), 90(5%), 89(13%).

Ultraviolet absorption spectrum (EtOH);

$\nu$max=201(35,000), 217$^{sh}$(12,200), 228$^{sh}$(8,340), 277$^{sh}$(1,120), 285(1,650), 292(1,470)nm Elementary analysis;

calculated as C$_{15}$H$_{14}$Cl$_3$NO C:54.49 H:4.27 N:4.24(%) Found; C:54.61 H:4.38 N:4.01(%) ,

EXAMPLE 3

Synthesis of N-4-chlorobenzyl-N-2-(3,4-dichlorophenoxy)ethylammonium p-toluene sulfonate (compound No. 82).

The compound was synthesized in two steps as described below.

1) Synthesis of N-4-chlorobenzyl-N-2-(3,4-dichlorophenoxy)ethylamine 2.70 Grams (10.0 mmol) of 2-(3,4dichlorophenoxy)ethyl bromide was dissolved in 30 ml of ethanol, followed by the addition of 1.06 g (10.0 mmol) of anhydrous sodium carbonate and 4.25 g (30.0 mmol) of 4-chlorobenzylamine. The mixture was heated and refluxed on an oil bath for 7 hours. After cooling, the reaction mixture was poured into 100 ml of water and was extracted with chloroform (20 ml×3).

The organic layer was dried over with magnesium sulfate and the solvent was removed by distillation, and the residue was purified by silica gel column chromatography ( developing agent: ethyl acetate/chloroform=4/6 ) to give the captioned compound in an amount of 2.99 g (yield, 90%) in the form of a colorless oil.

The compound exhibited the following properties.
Mass spectrum;

m/e=330(M$^+$+1.1%), 298(3%), 297(6%), 296(30%), 295(19%), 294(38%), 293(22%), 170(4%), 168(5%), 157(3%), 156(34% ), 155(8%), 154(92%), 127(44%), 126(8%), 125(100%), 90(7%), 89(20%).

Ultraviolet absorption spectrum (EtOH);

$\nu$max=218$^{sh}$ (13,200), 230$^{sh}$(8,340), 281$^{sh}$(1,200), 286(1,700), 292(1,500)nm Elementary analysis;

calculated as C$_{15}$H$_{14}$Cl$_3$NO C:54.49 H:4.27 N:4.24(%) Found; C:54.61 H:4.38 N:4.01(%)

2) Synthesis of N-4-chlorobenzyl- N-2-(3,4-dichlorophenoxy ) e thy lammonium- p-toluene sulfonate 331 Milligrams (1.00 retool) of the amine obtained in the above step 1) was dissolved in 2 ml of ether followed by the addition of 190 mg (1.00 mmol) of p-toluenesulfonic acid monohydrate. The acid was dissolved by ultrasonic treatment, and the newly precipitated crystals were separated by filtration, washed with ether and then dried to obtain 322 mg (yield, 80%) of the captioned compound in the form of colorless scale-like crystals, m.p., 170–171° C.

| Preparation Example 1 (Wettable Powder) | |
| --- | --- |
| Component | Amount (parts by weight) |
| Compound No. 8 | 20 |
| Lignin-sulfonic acid | 3 |
| Polyoxyethylene alkylaryl ether | 2 |

-continued

Preparation Example 1 (Wettable Powder)

| Component | Amount (parts by weight) |
|---|---|
| Diatomaceous earth | 75 |

The foregoing components homogeneously mixed to give a wettable powder comprising 20% by weight of the active ingredient.

Preparation Example 2 (Powder)

| Component | Amount (parts by weight) |
|---|---|
| Compound No. 8 | 3 |
| Calcium stearate | 1 |
| Powder of silicic acid anhydride | 1 |
| Clay | 48 |
| Talc | 47 |

The foregoing components were homogeneously mixed to give a powder comprising 3% by weight of the active ingredient.

Test 1 (Antibacterial Test against Phytopathogenic Bacteria

Antibacterial actions of the N-benzyl-N-phenoxyethylamine and N-benzyl-N-phenoxyethylamine salt against various phytopathogenic bacteria were examined.

More specifically, the bacterium causing black spot of cabbage, *Xanthomonas campestris* pv. *campestris*, the bacterium causing citrus canker, *X. Campestris* pv. *citri*, the bacterium causing bacterial leaf blight of rice, *X. Campestris* pv. *oryzae*, the bacterium causing bacterial shot hole of peach, *X. campestris* pv. *pruni* and the bacterium causing tomato canker, *Clavibacter michiganmensis* subsp. *michiganensis*, were used as the bacteria to be tested, and the action of inhibiting the growth of the bacteria on an agar plate was examined.

A sample compound was added to a peptone-added potato extract medium, and a 2-fold dilution system having a maximum concentration of 100 ppm was prepared and the culture medium was cast into a Petri dish to form an agar plate.

The agar plate was inoculated with the bacterium to be tested and incubation was carried out at 28° C. for 2 days, and the growth of the bacterium was checked.

The obtained results are shown in Table 3.

The compounds of the present invention showed a strong antibacterial action against all of the pathogenic bacteria.

TABLE 3

Antibacterial tests against phytopathogenic bacteria of plants
Minimum inhibition concentration (ppm)

| Compound No. | Xc | Xi | Xo | Xp | Cm |
|---|---|---|---|---|---|
| 1 | 25 | 25 | | | 25 |
| 2 | 25 | 25 | | | 6.3 |
| 3 | 50 | 50 | | | 6.3 |
| 4 | 25 | 25 | | | 25 |
| 5 | 12.5 | 12.5 | 6.3 | 12.5 | 12.5 |
| 6 | 12.5 | 12.5 | 12.5 | 12.5 | 12.5 |
| 8 | 50 | 50 | | | 6.3 |
| 9 | 100 | 50 | | | 12.5 |
| 40 | 25 | 25 | | | 25 |
| 42 | 12.5 | 12.5 | 12.5 | 12.5 | 6.3 |
| 44 | 12.5 | 6.3 | 3.2 | 12.5 | 6.3 |

TABLE 3-continued

Antibacterial tests against phytopathogenic bacteria of plants
Minimum inhibition concentration (ppm)

| Compound No. | Xc | Xi | Xo | Xp | Cm |
|---|---|---|---|---|---|
| 51 | 12.5 | 12.5 | 6.3 | 12.5 | 12.5 |
| C | 25 | 25 | 6.3 | 25 | 6.3 |

C: Streptomycin (commercially available comparative agent)
Xc: Bacteria causing black spot of cabbage
Xi: Bacteria causing citrus canker
Xo: Bacteria causing bacterial leaf blight of rice
Xp: Bacteria causing bacterial shot hole of peach
Cm: Bacteria causing tomato canker Test 2 (Test of Preventing Citrus Canker)

Leaf pieces having a square shape of about 1 cm$^2$ were cut out from summer orange leaves and immersed in a chemical solution having a predetermined concentration for 20 minutes. The leaf pieces were removed from the chemical solution and were then air-dried. Then, the leaf pieces were inoculated with a suspension of cells of the bacterium causing citrus Canker (about 10$^8$ cells per ml) by using a needle.

The inoculated leaf pieces were placed in a Petri dish on which a sheet of wet filter paper was spread, and incubation was carried out at 28° C. for 10 days and the outbreak of the disease was checked. The disease attack ratio was calculated according to the following formula:

$$\text{Disease attack ratio (\%)} = \frac{0Xn_0 + 1Xn_1 + 2Xn_2 + 3Xn_3}{3 \times N} \times 100$$

wherein $n_0$ represents the number of leaf pieces having a disease severity index of 0 (no disease), $n_1$ represents the number of leaf pieces having a disease severity index of 1 (slight disease), $n_2$ represents the number of leaf pieces having a disease severity index 2 (medium disease), $n_3$ represents the number of leaf pieces having a disease severity index of 3 (violent disease), and N represents the total number of the examined leaf pieces.

Furthermore, the degree of phytotoxicity was visually examined.

The results were as shown in Table 4.

TABLE 4

| Compound No. | Test for preventing citrus canker | | Phytotoxicity** |
|---|---|---|---|
| | Concentration (ppm) | Disease attack ratio (%) | |
| 1 | 300 | 23.8 | |
| 2 | 300 | 20.8 | — |
| 3 | 300 | 7.4 | — |
| 4 | 300 | 20.8 | — |
| 5 | 300 | 14.3 | — |
| 6 | 300 | 16.7 | — |
| 7 | 300 | 14.3 | — |
| 8 | 300 | 7.4 | — |
| 9 | 300 | 9.5 | — |
| 10 | 300 | 14.3 | — |
| 39 | 300 | 16.7 | — |
| 40 | 300 | 13.3 | — |
| 41 | 300 | 16.7 | — |
| 42 | 300 | 7.4 | — |
| 43 | 300 | 0.0 | — |
| 44 | 300 | 0.0 | — |
| 50 | 300 | 4.8 | — |
| cocide wettable powder* | diluted to 1/2000 2000 | 26.7 | ± |

TABLE 4-continued

| Test for preventing citrus canker | | | |
|---|---|---|---|
| Compound No. | Concentration (ppm) | Disease attack ratio (%) | Phytotoxicity** |
| untreated | | 66.7 | |

*Commercially available comparative agent.
**—: No phytotoxicity.
±: Phytotoxic to a slight degree.
+: Phytotoxic (hereinafter the same).

Test 3 (Test of Controlling Bacterial Leaf Blight of Rice).

An aqueous solution containing a sample compound at a predetermined concentration was sprayed onto the rice plants of the 5-leaf stage (variety: Koshihikari) grown in a pot having a diameter of 6 cm.

After one day has passed, the rice plants were shear-inoculated with a cell suspension of the bacterium causing bacterial leaf blight of rice, which had a concentration of $10^8$ cells per ml.

Three weeks after the inoculation, the lengths of disease lesions were measured, and the control values were calculated according to the following formula:

$$\text{Control value (\%)} = \left(1 - \frac{\text{average disease lesion length in treated leaf}}{\text{average disease lesion length in untreated leaf}}\right) \times 100$$

The obtained results were as shown in Table 5.

TABLE 5

| Test for controlling bacterial leaf blight of rice | | | |
|---|---|---|---|
| Compound No. | Concentration (ppm) | Control value (%) | Phytotoxicity |
| 3 | 500 | 80.5 | — |
| 8 | 500 | 75.6 | — |
| 9 | 500 | 88.2 | — |
| 40 | 500 | 83.7 | — |
| 42 | 500 | 90.0 | — |
| 43 | 500 | 95.1 | — |
| 44 | 500 | 96.3 | — |
| phenazine wettable powder* | diluted to 1/500 | 60.1 | — |

*Commercially available comparative agent.

Test 4 (Test of Controlling Soft Rot)

Radish disks having a diameter of 2 cm and a thickness of 1 cm were prepared and immersed in an aqueous solution containing a sample compound at a predetermined concentration for 1 hour.

The radish disks were taken out from the aqueous solution and air-dried. A bacterium suspension was dropped on central portions of the disks and the disks were maintained at 28° C. for 24 hours. The rotted degree was examined and the control values were calculated according to the following formula:

$$\text{Control value (\%)} = \left(1 - \frac{\text{number of rotted disks}}{\text{number of examined disks}}\right) \times 100$$

The results were as shown in Table 6.

TABLE 6

| Test of controlling soft rot | | | |
|---|---|---|---|
| Compound No. | Concentration (ppm) | Control value (%) | Phytotoxicity |
| 3 | 400 | 90 | — |
| 8 | 400 | 90 | — |
| 43 | 400 | 100 | — |
| 44 | 400 | 100 | — |
| cocide wettable powder* | diluted to 1/2000 | 80 | ± |

*Commercially available comparative agent.

Test 5 (Antibacterial Test against phytopathogenic Bacteria

Antibacterial actions of the N-benzyl-N-dichlorophenoxyethylamines and of salts of organic acids against various phytopathogenic bacteria were examined.

More specifically, the bacterium causing black spot of cabbage, *Xanthomonas campestris* pv. *campestris*, the bacterium causing citrus canker, *X. campestris* pv. *citri*, the bacterium causing bacterial leaf blight of rice, *X. campestris* pv. *oryzae*, the bacterium causing bacterial shot hole of peach, *X. campestris* pv. *pruni*, and the bacterium causing tomato canker, *Clavibacter michiganensis* subsp. *michiganensis*, were tested to examine the action of inhibiting the growth of the bacteria on an agar plate.

The sample compound was added to a peptone-added potato extract medium, and a 2-fold dilution system having a maximum concentration of 100 ppm was prepared and the culture medium was cast into a Petri dish to form an agar plate.

The agar plate was inoculated with the bacterium to be tested and incubation was carried out at 28° C. for two days to examine the growth of the bacterium.

The results were as shown in Table 7.

The compounds of the present invention exhibited a strong antibacterial action against all of the pathogenic bacteria.

TABLE 7

| Antibacterial tests against phytopathogenic bacteria of plants Minimum inhibition concentration (ppm) | | | | | |
|---|---|---|---|---|---|
| Compound No. | Xc | Xi | Xo | Xp | Cm |
| 83 | 12.5 | 12.5 | 6.3 | 6.3 | 12.5 |
| 86 | 6.3 | 6.3 | 3.2 | 3.2 | 6.3 |
| 87 | 6.3 | 6.3 | 3.2 | 3.2 | 6.3 |
| 88 | 6.3 | 6.3 | 3.2 | 3.2 | 12.5 |
| 89 | 6.3 | 6.3 | 6.3 | 3.2 | 6.3 |
| 90 | 12.5 | 12.5 | 12.5 | 12.5 | 12.5 |
| 91 | 12.5 | 12.5 | 6.3 | 6.3 | 3.2 |
| 92 | 25 | 12.5 | 12.5 | 12.5 | 6.3 |
| 93 | 12.5 | 12.5 | 6.3 | 12.5 | 6.3 |
| streptomycin* | 25 | 25 | 6.3 | 25 | 6.3 |

*Commercially available comparative agent.
Xc: Bacteria causing black spot of cabbage
Xi: Bacteria causing citrus canker
Xo: Bacteria causing bacterial leaf blight of rice
Xp: Bacteria causing bacterial shot hole of peach
Cm: Bacteria causing tomato canker Test 6 (Prevention of Citrus Canker)

Leaf pieces having a square of about 1 cm² were cut out from summer orange leaves and immersed in a chemical solution having a predetermined concentration for 20 minutes. The leaf pieces were taken out from the chemical solution and were then air-dried. Then, the leaf pieces were inoculated with a suspension of cells of the bacterium causing citrus canker (about $10^8$ cells per ml) by using a needle. The inoculated leaf pieces were placed in a Petri dish on which was spread a sheet of wet filter paper, and incubation was carried out at 28° C. for 10 days and the outbreak of the disease was examined. The disease attack ratio was calculated according to the following formula:

$$\text{Disease attack ratio (\%)} = \frac{0 X n_0 + 1 X n_1 + 2 X n_2 + 3 X n_3}{3 \times N} \times 100$$

wherein $n_0$ represents the number of leaf pieces having a disease severity index of 0 (no disease), $n_1$ represents the number of leaf pieces having a disease severity index of 1 (slight disease), $n_2$ represents the number of leaf pieces having a disease severity index of 2 (medium disease), $n_3$ represents the number of leaf pieces having a disease severity index of 3 (violent disease), and N represents the total number of the examined leaf pieces.

Furthermore, the degree of phytotoxicity was visually examined.

The results were as shown in Table 8.

TABLE 8

| | Test for preventing citrus canker | | |
|---|---|---|---|
| Compound No. | Concentration (ppm) | Disease attack ratio (%) | Phytotoxicity** |
| 79 | 300 | 16.7 | — |
| 80 | 300 | 7.4 | — |
| 81 | 300 | 9.5 | — |
| 82 | 300 | 14.3 | — |
| 84 | 300 | 16.7 | — |
| 85 | 300 | 13.3 | — |
| 86 | 300 | 16.7 | — |
| 87 | 300 | 0.0 | — |
| 88 | 300 | 0.0 | — |
| 89 | 300 | 20.8 | — |
| 90 | 300 | 7.4 | — |
| 92 | 300 | 20.8 | — |
| 93 | 300 | 4.8 | — |
| cocide wettable powder* | diluted to 1/2000 2000 | 26.7 | ± |
| untreated | | 66.7 | |

*Commercially available comparative agent.
**—: No phytotoxicity.
±: Phytotoxic to a slight degree.
+: Phytotoxic (hereinafter the same).

Test 7 (Test of Controlling Bacterial Leaf Blight of Rice)

An aqueous solution containing a sample compound at a predetermined concentration was sprayed onto the rice plants of the 5-leaf stage (variety: Koshihikari) grown in a pot having a diameter of 6 cm.

One day after, the rice plant was shear-inoculated with a cell suspension of the bacterium causing bacterial leaf blight of rice having a concentration of $10^8$ cells per milliliter.

Three weeks after the inoculation, the lengths of disease lesions were measured, and the control values were calculated according to the following formula:

$$\text{Control value (\%)} = \frac{\text{average disease lesion length in treated leaf}}{\text{average disease lesion length in untreated leaf}} \times 100$$

The results were as shown in Table 9.

TABLE 9

| | Test for controlling bacterial leaf blight of rice. | | |
|---|---|---|---|
| Compound No. | Concentration (ppm) | Control value (%) | Phytotoxicity |
| 80 | 500 | 83.7 | — |
| 84 | 500 | 95.1 | — |
| 85 | 500 | 80.5 | — |
| 86 | 500 | 75.6 | — |
| 87 | 500 | 90.0 | — |
| 89 | 500 | 88.2 | — |
| 93 | 500 | 96.3 | — |
| phenazine wettable powder* | diluted to 1/500 | 60.1 | — |

*Commercially available comparative agent.

Test 8 (Test of Controlling Soft Rot)

Radish disks having a diameter of 2 cm and a thickness of 1 cm were prepared and immersed in an aqueous solution containing a sample compound at a predetermined concentration for 1 hour.

The radish disks were taken out from the aqueous solution and were air-dried. A bacterium suspension was dropped on central portions of the disks and the disks were maintained at 28° C. for 24 hours to examine the rotted degree. The control values were calculated according to the following formula:

$$\text{Control value (\%)} = \frac{\text{number of rotted disks}}{\text{number of examined disks}} \times 100$$

The results were as shown in Table 10.

TABLE 10

| | Test of controlling soft rot. | | |
|---|---|---|---|
| Compound No. | Concentration (ppm) | Control value (%) | Phytotoxicity |
| 80 | 400 | 90 | — |
| 86 | 400 | 100 | — |
| 89 | 400 | 90 | — |
| 93 | 400 | 100 | — |
| cocide wettable powder* | diluted to 1/2000 | 80 | |

*Commercially available comparative agent.

The N-benzyl-N-phenoxyethylamines and salts thereof of the present invention are all novel compounds that can be easily prepared, featuring stable properties and exhibiting excellent antibacterial action against various pathogenic bacteria of plants. Therefore, the agricultural and horticultural agent of the present invention can be desirably used for controlling a variety of plant diseases.

We claim:

1. An N-benzyl-N-phenoxyethylamine selected from the group consisting of the N-benzyl-N-phenoxyethylamine represented by the following formula (I):

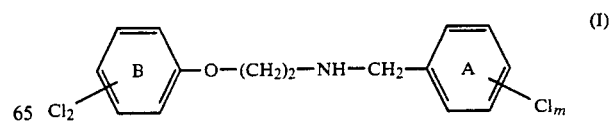

and an agriculturally acceptable acid addition salt represented by the following formula (II):

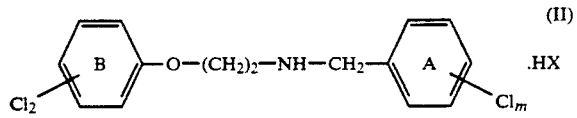
(II)

wherein m represents a number of 1 or 2 with a proviso that when m is 1 and a chlorine atom in the ring A is present at para(4)-position of the ring A, two chlorine atoms in the ring B are present at 2,3-, 2,5-, 2,6-, 3,4- or 3,5-positions of the ring B, and HX represents an acid.

2. An N-benzyl-N-phenoxyethylamine according to claim 1 which is represented by the following formula III, IV, V or VI or an agriculturally acceptable acid addition salt thereof:

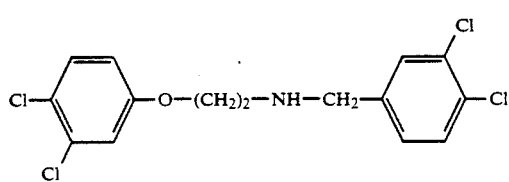
(III)

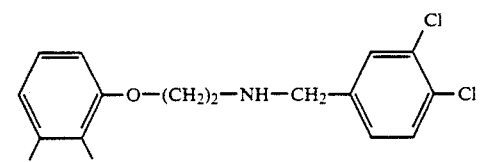
(IV)

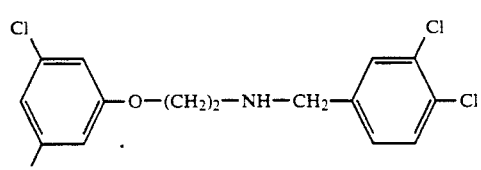
(V)

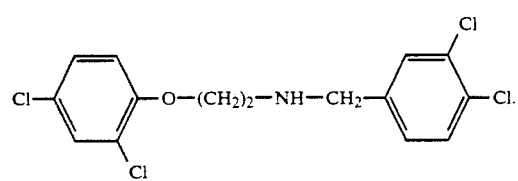
(VI)

3. A horticultural and agricultural bactericidal composition for preventing and/or curing plant disease, wherein said composition comprises (A) as an active ingredient, at least one member selected from the group consisting of the N-benzyl-N-phenoxyethylamine represented by the following formula (I'):

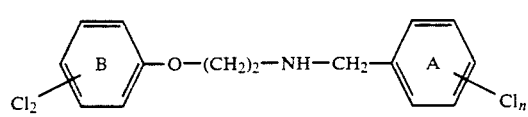
(I')

and an agriculturally acceptable acid addition salt represented by the following formula (II'):

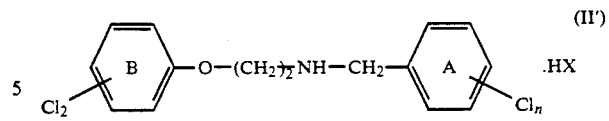
(II')

wherein n is a number of 1 or 2, and HX represents an acid and (B) at least one of agriculturally acceptable carriers.

4. The composition according to claim 3 wherein said active ingredient is at least one member selected from the group consisting of the N-benzyl-N-phenoxyethylamine represented by the following formula (I):

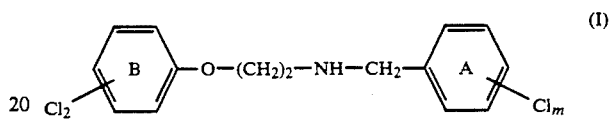
(I)

and an agriculturally acceptable acid addition salt represented by the following formula (II):

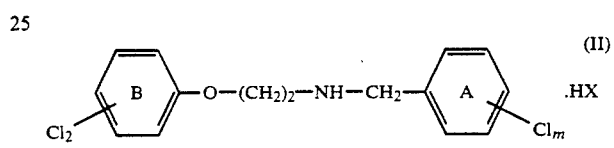
(II)

wherein m represents a number of 1 of 2 with a proviso that when m is 1 and a chlorine atom in the ring A is present at para(4)-position of the ring A, two chlorine atoms in the ring B are present at 2,3-, 2,5-, 2,6-, 3,4- or 3,5-positions of the ring B, and HX represents an acid.

5. A horticultural and agricultural bactericidal composition for preventing and/or curing plant diseases, wherein said composition comprises as an active ingredient, at least one member selected from the group consisting of an N-benzyl-N-phenoxyethylamine represented by the following formula III, IV, V or VI and an agriculturally acceptable acid addition salt thereof, and at least one of agriculturally acceptable carriers,

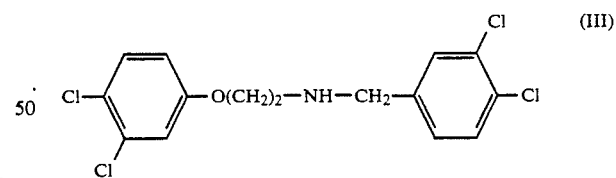
(III)

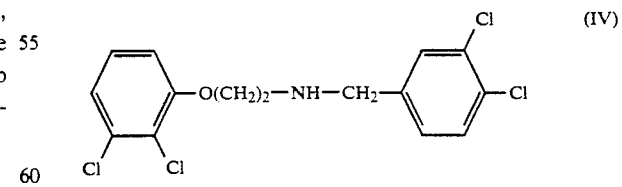
(IV)

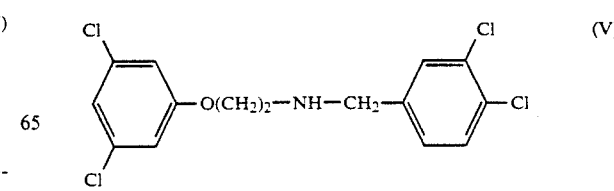
(V)

-continued

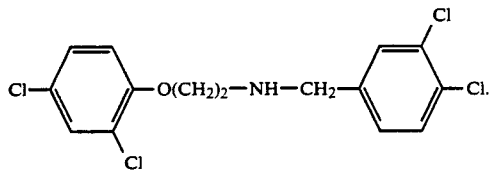

6. The composition according to claim 4 wherein the active ingredient is present in an amount of from about 0.001 to about 95% by weight, expressed as formula (I).

7. The composition according to claim 4 wherein the active ingredient is present in an amount of from about 0.01 to about 90% by weight, expressed as formula (I).

8. The composition according to claim 4 which is in the form of a powder, DL dust or a granule wherein the content of the active ingredient is about 0.01 to about 5% by weight.

9. The composition according to claim 4 which is in the form of a wettable powder, a liquid or an emulsifiable concentrate wherein the content of the active ingredient is about 1 to about 75% by weight.

10. A composition according to claim 3 comprising as an active ingredient, a compound represented by the following formula

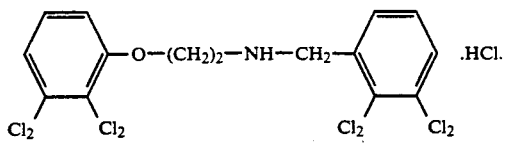

11. A composition according to claim 3 comprising as an active ingredient a compound represented by the following formula

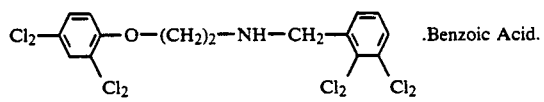

* * * * *